US007233145B2

United States Patent
Mueller et al.

(10) Patent No.: US 7,233,145 B2
(45) Date of Patent: Jun. 19, 2007

(54) METHOD FOR MAGNETIC RESONANCE IMAGING WITH CORRECTION FOR FLUCTUATIONS IN THE TRAMSISSION FIELD STRENGTH

(75) Inventors: Edgar Mueller, Heroldsbach (DE); Markus Vester, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 556 days.

(21) Appl. No.: 10/256,415

(22) Filed: Sep. 27, 2002

(65) Prior Publication Data

US 2003/0078491 A1 Apr. 24, 2003

(30) Foreign Application Priority Data

Sep. 28, 2001 (DE) ................................. 101 47 941

(51) Int. Cl.
*G01V 3/00* (2006.01)
(52) U.S. Cl. ........................ 324/314; 324/309; 324/307
(58) Field of Classification Search ................ 600/407, 600/410; 324/307, 314
See application file for complete search history.

(56) References Cited

U.S. PATENT DOCUMENTS

| | | | | |
|---|---|---|---|---|
| 4,993,075 A | * | 2/1991 | Sekihara et al. ............ 382/131 |
| 5,001,428 A | * | 3/1991 | Maier et al. ................ 324/309 |
| 5,262,945 A | * | 11/1993 | DeCarli et al. ............. 600/410 |
| 5,481,190 A | * | 1/1996 | Sugiura ..................... 324/314 |
| 6,049,206 A | * | 4/2000 | Sharp ........................ 324/314 |
| 6,552,541 B2 | * | 4/2003 | Nauerth ..................... 324/309 |
| 6,897,653 B2 | * | 5/2005 | Van Den Brink et al. .. 324/307 |
| 2002/0003422 A1 | * | 1/2002 | Nauerth ..................... 324/309 |
| 2003/0098688 A1 | * | 5/2003 | Brinker et al. ............. 324/309 |
| 2005/0017718 A1 | * | 1/2005 | Zwanenburg et al. ....... 324/309 |

FOREIGN PATENT DOCUMENTS

EP 0 391 279 10/1990

* cited by examiner

*Primary Examiner*—Brian L. Casler
*Assistant Examiner*—John F. Ramirez
(74) *Attorney, Agent, or Firm*—Schiff Hardin LLP

(57) ABSTRACT

In a method for magnetic resonance imaging, whereby magnetic resonance signals in a region of interest of an examination subject are generated in an examination by applying radio-frequency pulses of a first transmission field strength and the magnetic resonance signals are acquired in a spatially coded manner and allocated to volume elements of the region of interest in order to obtain one or more magnetic resonance images of the region of interest, the sensitivity of each volume element of the region of interest with respect to a modification of the first transmission field strength is determined, deviations of the first transmission field strength from a reference field strength are measured during the examination, and the magnetic resonance signals acquired in the examination are corrected on the basis of the sensitivity determined for each volume element and on the basis of the measured deviations of the first transmission field strength from the reference field strength. The method enables the implementation of fMRI measurements with high precision given fluctuating transmission field strength.

15 Claims, 4 Drawing Sheets

METHOD FOR MAGNETIC RESONANCE IMAGING WITH CORRECTION FOR FLUCTUATIONS IN THE TRAMSISSION FIELD STRENGTH

BACKGROUND OF THE INVENTION

1. Field of the Invention

The present invention is directed to a method for magnetic resonance (MR) imaging that can be particularly utilized for the implementation of sensitive magnetic resonance measurements wherein a fluctuating transmission field strength has a negative influence.

2. Description of the Prior Art

Magnetic resonance tomography is a known technique for acquiring images of the inside of the body of a living examination subject. For the implementation of magnetic resonance tomography, a basic field magnet generates a static, relatively homogeneous basic magnetic field. During the registration of magnetic resonance images, rapidly switched gradient fields for location coding are superimposed on this basic magnetic field, these gradient fields being generated by gradient coils. Radio-frequency pulses having a defined transmission field strength $B_1$ for triggering magnetic resonance signals S are emitted into the examination subject with radio-frequency transmission antennas. The magnetic resonance signals produced with these radio-frequency pulses are picked up by radio-frequency reception antennas. The magnetic resonance images of the examined subject region of the examination subject are produced on the basis of these magnetic resonance signals received with the reception antennas. Each picture element in the magnetic resonance image is allocated to a small body volume, referred to as the voxel. The brightness or intensity value of the picture element is dependent on the signal amplitude of the magnetic resonance signal received from this voxel. The intensity of the magnetic resonance signal S is in turn dependent on the intensity of the emitted field $B_1$ of the radio-frequency transmission antennas, among other things.

The exciting transmission field strength $B_1$ cannot be kept precisely constant due to unavoidable fluctuations in the transmission power, for example due to temperature fluctuations or disturbances in the amplifier as well as the properties of the transmission antenna, for example due to heating or a change in capacitance given movements on the part of the patient. The effects of a fluctuating transmission field strength are disturbing particularly when sensitive measurements wherein extremely minute signal differences in the magnetic resonance signals are of significance. An example of such a measurement is functional magnetic resonance imaging (fMRI) with which information about the brain activity in humans and animals can be obtained. In functional magnetic resonance tomography, magnetic resonance exposures of the subject volume to be examined, the brain of a patient, are made at short time intervals. A stimulus-specific neural activation can be detected and spatially localized by comparing the signal curve measured with the means of functional imaging for each volume element of the subject volume to the time curve of a model function. Since the minute changes of the received magnetic resonance signal triggered by physiological events must thereby be detected, functional magnetic resonance imaging requires an extremely high stability of the magnetic resonance system. Fluctuations in the transmission field strength can greatly degrade the analytical validity of the measurements.

Two different concepts are currently known for countering this known problem of the fluctuating transmission field strength in measurements of functional magnetic resonance tomography. One approach employs class-A transmission amplifiers as the antenna transmission amplifiers. These offer a high stability of the amplification in order to achieve an optimally constant transmission field strength during the measurement. These transmission amplifiers, however, are extremely complicated technically and also exhibit a poor efficiency.

It is also known to place a reference object in the form of a phantom object next to the examination subject in the measurement field or measurement volume (FOV=field of view) during the measurement, a reference signal being obtained from this reference object. The magnetic resonance signals received from the volume elements (voxels) of the examination subject are then referenced to this reference signal in order to correct fluctuations of the transmission field strength in the magnetic resonance signals. This technique, however, is only meaningful given a repetition time TR of the excitation that is far longer than the longest longitudinal relaxation time T1 (usually about 1 second) occurring in the tissue of the examination subject, since the signal S of a volume element is then proportional to $\sin(\alpha)$, whereby $\alpha \sim B_1$, so that S correlates directly with the transmission field strength $B_1$. Due to the saturation of the spin, the maximum of the signal then appears at $\alpha < 90°$, and the relationship between the signal S and the transmission field strength $B_1$ becomes dependent on the type of tissue of the respective volume element. In this case, the longitudinal relaxation time T1 of the phantom cannot be representative for the overall measurement volume. Moreover, a different mix of a number of signal-generating materials is present within each and every volume element, so that a simple allocation of the macroscopic tissue type to an effective T1 generally is not possible.

SUMMARY OF THE INVENTION

An object of the present invention is to provide a method for magnetic resonance imaging that enables a correction of the measured magnetic resonance signals without limitation given fluctuating transmission field strength.

This object is achieved in accordance with the invention in a method, wherein the sensitivity of each voxel r of the region of interest, with respect to the transmission field strength in the measurement field or measurement volume, is identified before, during or after the implementation of a magnetic resonance examination. The measured values, i.e. the measured magnetic resonance signals S, are then corrected on the basis of the sensitivity determined for each voxel r and the respectively measured deviation of the transmission field strength $B_1$ from a reference field strength $B_{10}$. The reference field strength $B_{10}$ can correspond, for example, to the initial value of the transmission field strength $B_1$ at the start of the examination.

As used herein "measurement" means the application of one or more radio-frequency pulses or radio-frequency pulse sequences as well as the acquisition of the magnetic resonance signals generated as a result thereof. The examination of a patient by applying radio-frequency pulses and acquiring the triggered magnetic resonance signals for generating one or more magnetic resonance images of a region of interest is also referred to below as the main measurement.

In an alternative of the present method, the determination of the sensitivity of each voxel ensues by means of at least one additional magnetic resonance measurement, referred to below as a calibration measurement, that is implemented with identical sequence parameters to those of the main measurement, but with two different transmission field strengths. The two different transmission field strengths lie in the region of the rated field strength $B_{10}$ intended for the main measurement. For example, one of the two transmission field strengths can lie above and the other can lie below the rated field strength $B_{10}$. Of course, one transmission field strength of the calibration measurement also can exhibit the value of the rated field strength $B_{10}$. In this calibration measurement, thus, at least two datasets or magnetic resonance images are obtained with magnetic resonance signals that differ in transmission field strength. The difference $\Delta B$ of the transmission field strengths with which the calibration measurement is implemented must lie above a value at which physiological effects can be left out of consideration for the calibration. Moreover, the difference should lie within a value range that still allows a linear approximation of the dependency of the magnetic resonance signal on the transmission field strength. Preferably, the difference $\Delta B$ of the transmission field strengths lies in a range of $\Delta B/B_{10}$ of approximately 20%.

By linear approximation, a sensitivity $s(r)=\Delta S(r)/\Delta B$ for each voxel r can be determined from the measured magnetic resonance signals of each voxel r that were measured in the calibration at the different, known transmission field strengths. A corrected signal value $$S_{korr}(r, t)=S(r, t)-s(r)*\Delta B_1(t)$$

that is independent of the fluctuations of the transmission field strength $B_1$ thus can be determined for each voxel r by multiplication of this sensitivity by the magnetic resonance signal measured during the main measurement and the likewise measured deviation $\Delta B_1(t)$ of the transmission field strength $B_1$ from the rated field strength $B_{10}$.

Of course, the calibration measurement can be implemented with more than two different transmission field strengths, so that higher order derivatives of the sensitivity going beyond the linear approximation can also be determined. This also enables a non-linear correction of the measured values. Thus, for example, a sensitivity of the first order can be determined by $s_1(r)=dS(r)/dB$ and a sensitivity of the second order can be determined by $s_2(r)=d^2s(r)/dB^2$. The magnetic resonance signals are then corrected in the following way:

$$S_{korr}(r, t)=S(r)-s_1(r)*\Delta B_1(t)-s_2(r)*\Delta B_1(t)^2/2.$$

In the simplest case, the calibration measurement is implemented for the same slice of the examination subject that is measured during the main measurement. When the calibration measurement is implemented before or after the main measurement, then the exact allocation of the voxel-dependent calibration data and the measured magnetic resonance signals can be lost given movements by the patient between the calibration and the main measurement. In order to avoid this, the calibration data are acquired as a complete 3D dataset over a larger measurement volume in one embodiment of the present method. The sensitivities at the image voxel positions actually acquired in the main measurement then can be linearly interpolated from this 3D dataset. The time duration of the imaging lengthened by the calibration is of no consequence in functional magnetic resonance imaging, with the typically long measuring times thereof.

Additional calibration data for at least two different repetition times TR also can be acquired in the calibration measurement, so that two sensitivities for each voxel are determined—a sensitivity $s_B$ dependent on the transmission field strength and a sensitivity $s_{TR}$ dependent on the repetition time TR. This also enables a correction of measurements with variable repetition times $TR_1$ as can occur in fMRI image sequences. In this application, an interpolation for the respective repetition time $TR_1$ of the main measurement is implemented from the identified sensitivities $s_{TR}$. The magnetic resonance signals are corrected in the following way on the basis of the two sensitivities:

$$S_{korr}(r, t)=S(r, t)-s_B(r)*\Delta B_1(t)-s_{TR}(r)*\Delta TR_1(t).$$

This enables the correction of measurements wherein the repetition rate TR is determined by external events via external trigger signals that, for example, are triggered by the heartbeat or the breathing of the patient. The time scale of the variation of the repetition time must be similar in calibration and imaging. It must either ensue so slowly that the spins in the calibration measurement are always nearly in equilibrium—when this also corresponds to the actual measuring situation of the main measurement—or a sudden deviation $\Delta TR$ must ensue in the calibration given an otherwise identically repeated sequence, when this situation is also present in the main measurement.

The calibration measurement can ensue at different times with reference to the actual magnetic resonance imaging. For example, it can be implemented before or after the main measurement. For longer magnetic resonance image sequences, the acquisition of the calibration data alternatively be temporally between the acquisition of the individual magnetic resonance images of the main measurement, for example at periodic intervals, or after a patient movement was detected.

In another alternative of the present method, an acquisition of the calibration data is realized by the main measurement itself. This ensues by means of intentional, systematic variation of the transmission field strength during the main measurement, for example periodically or according to a pseudo-random sequence, so that a dataset is acquired that contains the measured signals for the main measurement as well as the calibration data. The calibration data can then be separated from the actual physiological payload signal by correlation of the received data with the known variation of the transmission field strength, which should again not upwardly or downwardly exceed a certain size. As a result, the calibration data can be constantly updated during long measurements. The main measurement is hardly disturbed by the intentionally inserted variation due to the application of the correction with the sensitivities already acquired during the course of the main measurement. In this alternative, at least one calibration measurement for the initial determination of the sensitivity of the individual voxels preferably is implemented before the implementation of the main measurement. The temporally first magnetic resonance signals or image data are then corrected on the basis of these sensitivities and the simultaneously measured transmission field strength. As a result of the new calibration data constantly acquired during the main measurement, these sensitivities are then adapted to any modified boundary conditions which may occur, so that the following magnetic resonance signals are corrected on the basis of the currently determined sensitivities.

The correction of the magnetic resonance signals with the acquired sensitivities and the acquired variation of the transmission field strength can, given implementation of the calibration measurement before or during the actual measurement, ensue quasi in real time or only after the acquisition of all measured data.

The present method can be especially advantageously utilized in fMRI measurements wherein the minutest signal changes during a longer measurement duration are of great significance. The use of a high-stability transmission amplifier is not required. Further, the present method is independent of the type of tissue, so that no tissue-dependent errors can occur.

The measurement of the transmission field strength that is actually generated can ensue in a variety of ways. For example, the transmission field strength can be acquired by introducing a field probe into the transmission resonator, the signal thereof being received during the measurement. Such a field probe can be composed of a simple wire loop.

Further, an RF directional coupler can be inserted between the transmission amplifier and the transmission antenna for acquiring the transmission field strength. Given superimposition of RF forward and return signals weighted with suitable phase, a measured value thus can be acquired that is proportional to the antenna current, so that changes of the antenna properties such as resonance and quality also are acquired.

Another possibility for acquiring the transmission field strength is to insert a phantom with short T1 in the measurement field and to acquire the magnetic resonance signal thereof, the latter being proportional to the transmission field strength. This saves an additional measurement ADC (analog-to-digital converter) and the reservation of a reception channel during transmission. The use of a phantom, however, is sensitive for unstable gradient offsets, especially at the edge of the measurement field.

DESCRIPTION OF THE PREFERRED EMBODIMENTS

Figure 1:
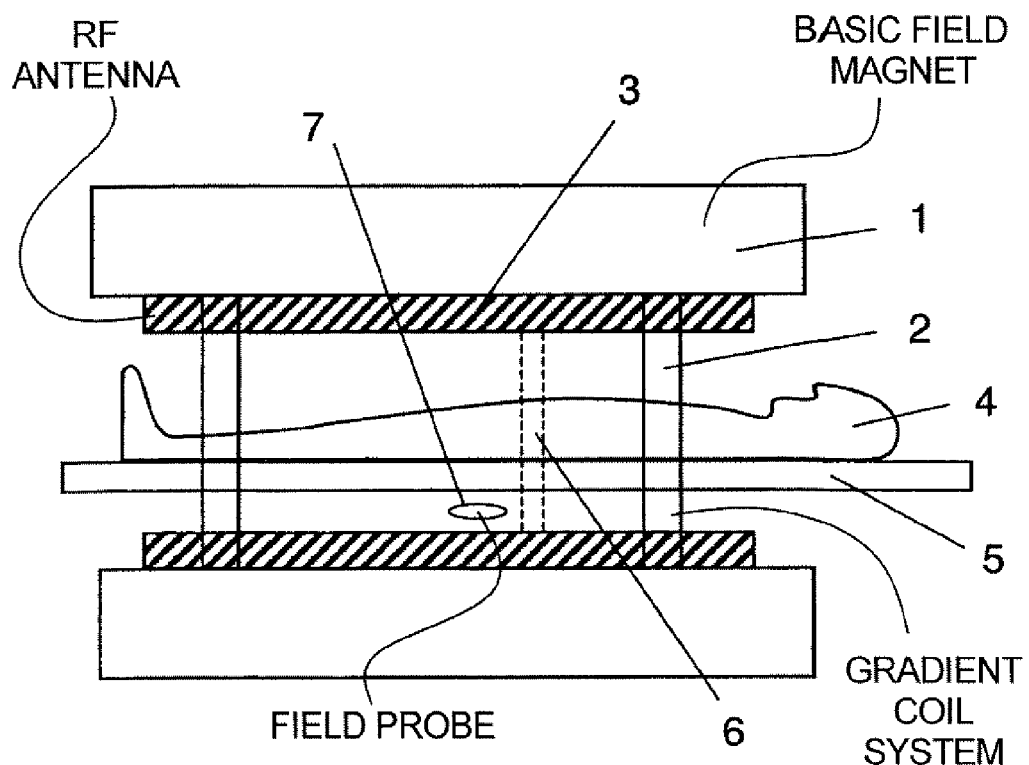
FIG. 1 schematically illustrates an example of the basic structure of a magnetic resonance tomography system, with which the inventive method can be implemented.

FIG. 1 schematically shows a magnetic conventional resonance tomography apparatus. FIG. 1 shows only the basic components of the apparatus: a basic field magnet 1, a gradient coil system 2, and a radio-frequency transmission and reception antenna 3. The radio-frequency transmission and reception antenna typically would be a head coil in fMRI measurements. A patient 4 also can be seen on a patient bed 5, the patient 4 representing the examination subject. In the measurement, one or more radio-frequency pulses for generating magnetic resonance signals are emitted into the body of the patient 4 via the radio-frequency transmission antenna 3, fashioned as a whole-body antenna, and the generated magnetic resonance signals that are acquired are presented in the form of a two-dimensional magnetic resonance image. In broken lines, FIG. 1 shows a slice 6 through the patient that is to be measured in the MR measurement. Further, a field probe 7 is shown with which the transmission field strength during a measurement is acquired.

Figure 2:
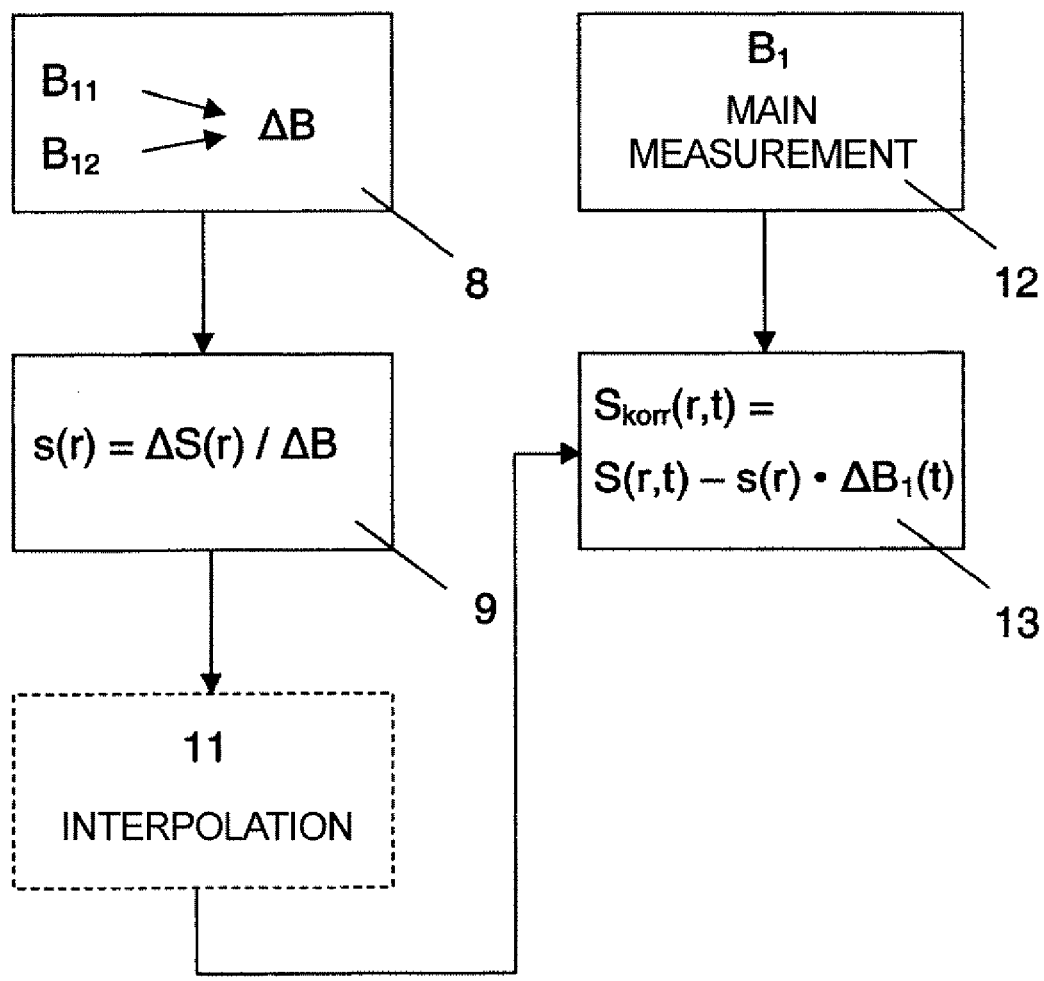
FIG. 2 is a flowchart illustrating a first embodiment of the inventive method.

As an example, FIG. 2 shows an embodiment of the present method for correcting a fluctuating transmission field strength during an fMRI measurement. In this method, a calibration 8 of the sensitivity of each volume element or voxel first ensues in the slice 6 to be measured or in a larger volume region containing this slice. In this calibration measurement 8, at least two calibration images are implemented with exactly the same sequence parameters as in the main measurement 12, i.e. FOV, slice position and TR (steady-state, i.e. the measured data are registered only after an equilibrium of the longitudinal magnetization has been established). The measurement of the calibration data, however, ensues with fields $B_{11}$ and $B_{12}$ appreciably deviating from the nominal $B_{10}$, (such as in a range between 15% and 25% of $B_{10}$) whereby $B^{12}-B_{11}=\Delta B$. "Appreciably" deviating means that $\Delta B / B_{10}$ is big enough in order to be able to neglect physiological effects for the calibration but small enough that $S(B_1)$ therein still can be linearly approximated. In the present case, a value of $\Delta_B/B_{10}=20\%$ is selected. The calibration data obtained from the measurement 8 are utilized in order to determine the sensitivities $s(r)=\Delta S(r)/\Delta B$ for each voxel r from the signal difference $\Delta S(r)$ of the two datasets obtained from the calibration measurement. Given exact measurement of the slice 6, a number of sensitivities $s(r)$ is thereby obtained that corresponds to the plurality of picture elements of the image matrix. A three-dimensional dataset is obtained given a measurement of a larger measurement volume.

Figure 5:
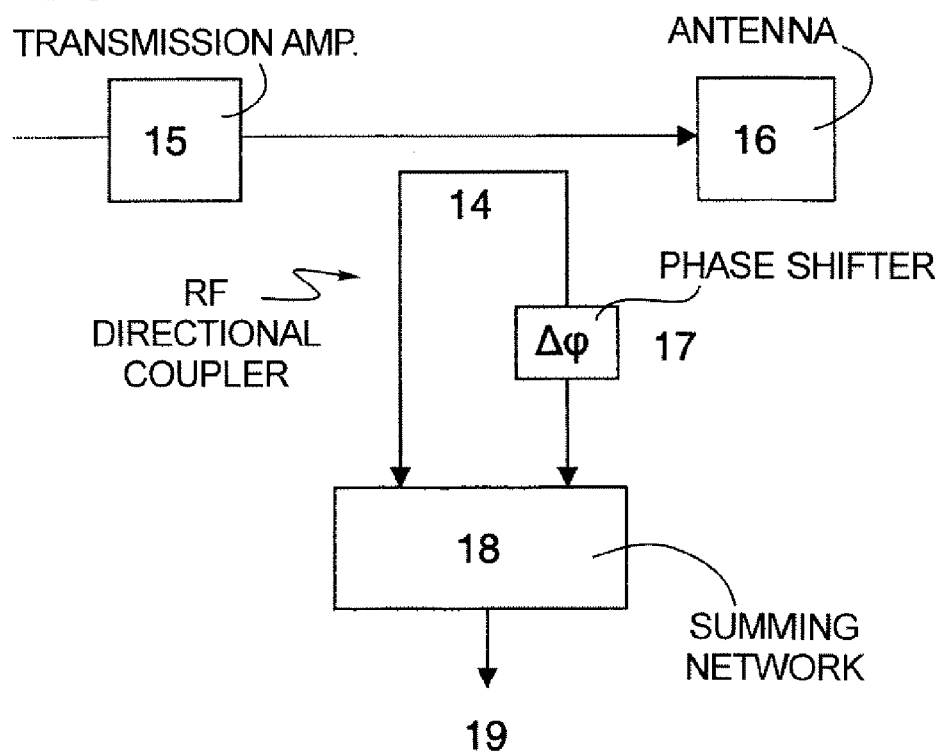
FIG. 5 is flowchart illustrating an example of the use of an RF directional coupler for acquiring the transmission field strength during the measurement, for use in the inventive method.

During the main measurement 12, the actual transmission amplitude $B_1(t)$ is acquired in addition to the acquisition of the measured data. This ensues via the field probe 7 shown in FIG. 1. The use of an RF directional coupler following the transmission amplifier also can be utilized for the acquisition of the transmission field strength $B_1(t)$, as shown in FIG. 5.

Finally, the measured values $S(r, t)$ acquired during the measurement 12 are corrected with the sensitivity $s(r)$ determined in the calibration measurement 8 in order to obtain a corrected intensity $S_{korr}(r, t)=S(r, t)-s(r)*\Delta B_1(t)$ for each voxel (step 13).

If a 3D dataset is obtained in the calibration measurement 8 instead of identical slices, then the sensitivities of the voxels actually measured during the main measurement 12 are linearly interpolated.

In this example, the calibration measurement 8 can ensue before or after the actual measurement 12. An implementation of the calibration measurement 8 between the individual measurement sequences of the measurement 12 also is possible.

Figure 3:
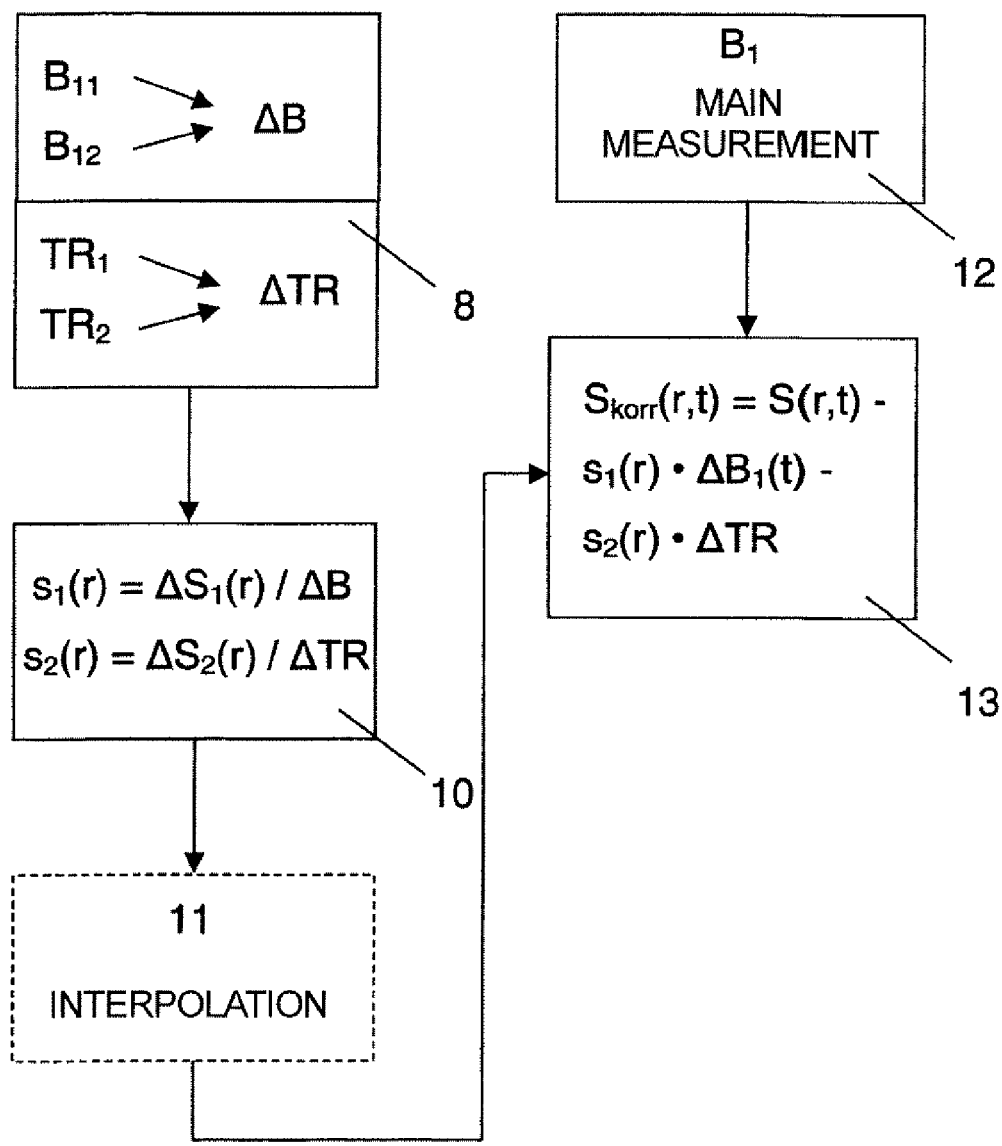
FIG. 3 is a flowchart illustrating a second embodiment of the inventive method.

Further, a calibration measurement 8 can be additionally implemented with two or more different repetition times TR. In this case, two sensitivities per voxel are obtained, as can be seen in FIG. 3 on the basis of step 10. In the interpolation step 11, the sensitivities that apply given the repetition rates TR occurring in the main measurement then are linearly interpolated.

Figure 4:
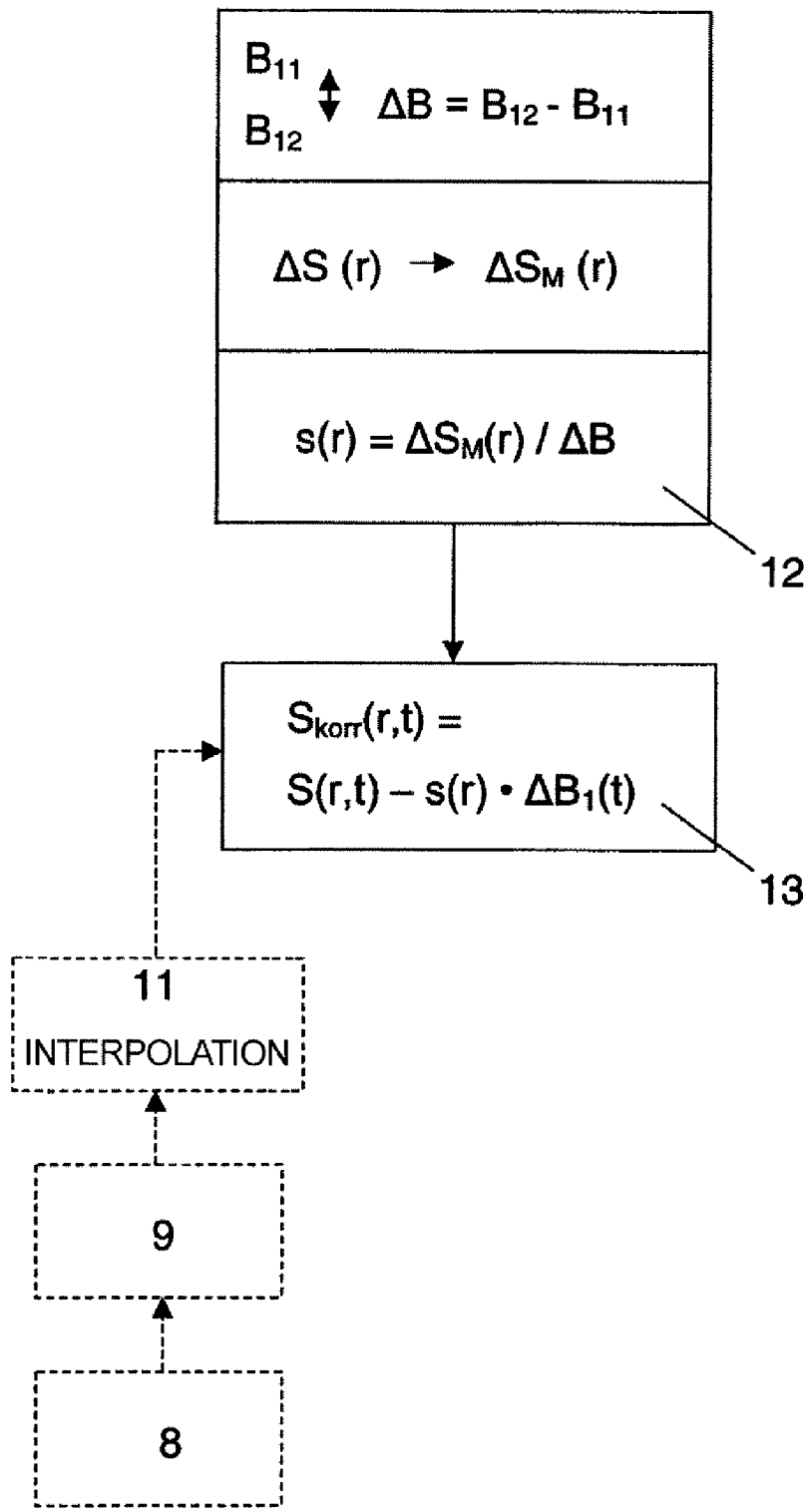
FIG. 4 is flowchart illustrating a third example of the inventive method.

FIG. 4 shows the procedure for an implementation of the calibration during the main measurement 12. In the present example, the RF transmission pulses are applied in alternation with higher and lower values of the transmission field strength, and the magnetic resonance signals as well as the respective transmission field strengths are measured. The differences $\Delta S(r)$ are formed from the measured data $S(r)$ acquired given the different transmission field strengths and the differences are averaged over a number of alternating periods of the transmission field strength. The sensitivities $s(r)=\Delta S_M(r)/\Delta B$ then are acquired from this average $\Delta S_M(r)$, whereby $\Delta B$ again corresponds to the difference between the applied transmission field strengths. The identified sensitivities again are utilized in order to obtain the measured data $S_{korr}(r, t)$ rid of the measured variation (large in this case) of the transmission field strength $\Delta B_{1cal}(t)$.

In this embodiment, the magnetic resonance signals acquired at the beginning of the main measurement remain uncorrected since sensitivities were not yet able to be determined.

In a version of this embodiment, a calibration according to the embodiment of FIG. 2 is therefore implemented before the main measurement. The first magnetic resonance signals then are corrected on the basis of this preceding calibration, and later magnetic resonance signals are corrected on the basis of the sensitivities that are determined or updated during the main measurement.

A constant updating of the calibration is possible in this way; as may be necessary due to movement on the part of the patient, for example given longer measuring times.

FIG. 5 shows an example of the acquisition of the fluctuating transmission field strength $B_1(t)$ by employing an RF directional coupler 14 following the transmission amplifier 15 for charging the antenna 16, which can correspond to the whole-body coil 3 of FIG. 1, with the required RF power. Via a phase shifter 17 and a summing network 18, the directional coupler 14 is connected to a reception channel 19 of the MR system, with which the exact transmission field strength is acquired.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for magnetic resonance imaging comprising the steps of:
    conducting a magnetic resonance examination of a subject by emitting radio-frequency signals, having a transmission field strength, into a region of interest, composed of a plurality of volume elements, of said subject and thereby exciting nuclear spins in said region of interest which generate magnetic resonance signals, and spatially encoding said magnetic resonance signals;
    determining a sensitivity of each of said volume elements in said region of interest to modification of said transmission field strength;
    during said examination, detecting deviations of said transmission field strength from a reference field strength;
    for each of said volume elements, correcting the magnetic resonance signals obtained therefrom dependent on said sensitivity and said deviations, to obtain corrected signals; and
    generating an image of said region of interest from said corrected signals.

2. A method as claimed in claim 1 wherein the step of determining said sensitivity comprises conducting at least one magnetic resonance measurement wherein radio-frequency signals are emitted into said region of interest with two different transmission field strengths.

3. A method as claimed in claim 2 comprising conducting said measurement before said examination.

4. A method as claimed in claim 2 comprising conducting said measurement after said examination.

5. A method as claimed in claim 2 wherein the step of emitting said radio-frequency signals in said examination comprises emitting said radio-frequency signals in successive pulse sequences, and comprising conducting said measurement between said pulse sequences.

6. A method as claimed in claim 2 comprising conducting said measurement by intentionally varying said transmission field strength of said radio-frequency signals emitted during said examination between said two different transmission field strengths.

7. A method as claimed in claim 2 wherein said measurement has physiological effects in said region of interest associated therewith, and comprising selecting said different transmission field strengths to differ by at least a value which allows said physiological effects to be neglected in determining said sensitivity.

8. A method as claimed in claim 2 wherein the step of correcting said magnetic resonance signals comprises correcting said magnetic resonance signals using a linear approximation, and comprising selecting said different transmission field strengths to deviate from said reference field strength only within a range which allows said linear approximation.

9. A method as claimed in claim 2 comprising selecting said different transmission field strengths to deviate from said reference field strength in a range between 15% and 25% of said reference field strength.

10. A method as claimed in claim 2 comprising conducting said examination to obtain magnetic resonance signals from at least one slice of said region of interest, and wherein the step of determining said sensitivity comprises determining the sensitivity of volume elements in said at least one slice.

11. A method as claimed in claim 2 comprising conducting said measurement for a plurality of slices in said region of interest to obtain a three-dimensional dataset, and wherein the step of correcting said magnetic resonance signals comprises correcting said magnetic resonance signals by interpolation from said three-dimensional dataset.

12. A method as claimed in claim 11 comprising correcting said magnetic resonance signals using non-linear interpolation.

13. A method as claimed in claim 1 wherein said sensitivity is a first sensitivity, and comprising the additional steps of:
    conducting a magnetic resonance measurement by varying a repetition time in said measurement between at least two different repetition times;
    determining a second sensitivity of said volume elements in said region of interest dependent on variation of said repetition time; and
    correcting said magnetic resonance signals dependent on said first sensitivity and said second sensitivity.

14. A method as claimed In claim 1 comprising detecting said deviation of said transmission field strength from said reference field strength during said examination using a field probe.

15. A method claimed in claim 1 comprising emitting said radio-frequency signals from a transmission antenna supplied by a transmission amplifier, and wherein the step of detecting said deviations of said transmission field strength from said reference field strength comprises connecting a directional coupler between said transmission antenna and said transmission amplfier.

* * * * *